United States Patent
Wang

(10) Patent No.: US 7,112,790 B1
(45) Date of Patent: Sep. 26, 2006

(54) METHOD TO PREPARE TEM SAMPLES

(75) Inventor: Naiyi Wang, Fremont, CA (US)

(73) Assignee: Cypress Semiconductor Corp., San Jose, CA (US)

( * ) Notice: Subject to any disclaimer, the term of this patent is extended or adjusted under 35 U.S.C. 154(b) by 133 days.

(21) Appl. No.: 10/898,532

(22) Filed: Jul. 23, 2004

Related U.S. Application Data

(60) Provisional application No. 60/494,817, filed on Aug. 13, 2003.

(51) Int. Cl.
*G01N 23/00* (2006.01)
*G21K 7/00* (2006.01)

(52) U.S. Cl. .................. 250/307; 250/440.11; 250/304

(58) Field of Classification Search .............. 250/307, 250/440.11, 304
See application file for complete search history.

(56) References Cited

U.S. PATENT DOCUMENTS 5,572,026 A * 11/1996 Ikeda .......................... 250/307
6,828,566 B1 * 12/2004 Tomimatsu et al. ..... 250/442.11

OTHER PUBLICATIONS

Liu et al., "A Methodology to Reduce Ion Beam Induced Damage in TEM Specimens Prepared by FIB," Int'l Symposium for Testing and Failure Analysis, Nov. 2002, pp. 313-316.*
Overwijk et al., "Novel scheme for the preparation of transmission electron microscopy specimens with a focused ion beam," J. Vac. Sci. Technol. B, vol. 11 No. 6, Nov./Dec. 1993, pp. 2021-2024.
Leslie et al., "TEM Sample Preparation Using FIB: Practical Problems and Artifacts," Int'l Symposium for Testing and Failure Analysis, Nov. 1995, pp. 353-362.
Rossie et al., "A Method for Thinning FIB Prepared TEM Specimens After Lift-Out," Microscopy & Microanalysis, vol. 7, Suppl. 2, pp. 940-941.
Liu et al., "A Methodology to Reduce Ion Beam Induced Damage in TEM Specimens Prepared by FIB," Int'l Symposium for Testing and Failure Analysis, Nov. 2002, pp. 313-316.
Young et al., "High-Yield and High-Throughput TEM Sample Preparation Using Focused Ion Beam Automation," Int'l Symposium for Testing and Failure Analysis, Nov. 1998, pp. 329-336.
Giannuzzi et al., "A review of focused ion beam milling techniques for TEM specimen preparation," Micron, vol. 30, 1999, pp. 197-204.

* cited by examiner

*Primary Examiner*—Jack Berman
*Assistant Examiner*—Jennifer Yantorno
(74) *Attorney, Agent, or Firm*—Mollie E. Lettang; Kevin L. Daffer; Daffer McDaniel, LLP

(57) ABSTRACT

A method for preparing a transmission electron microscopy (TEM) sample is provided which includes removing a portion of a substrate using a focused ion beam tool and securing the removed portion to a support structure to form a grafted structure. The method further includes forming an opening within the support structure to expose an underside of the removed portion and thinning the exposed underside using an ion beam miller tool. In some cases, the step of securing the removed portion to the support structure may include placing the substrate specimen upon a film attached to a mesh grid, positioning the mesh grid upon a framework comprising the support structure such that the substrate specimen is above the support structure, and pushing the substrate specimen through the film onto the support structure. A TEM sample resulting from such methods is also provided.

20 Claims, 4 Drawing Sheets

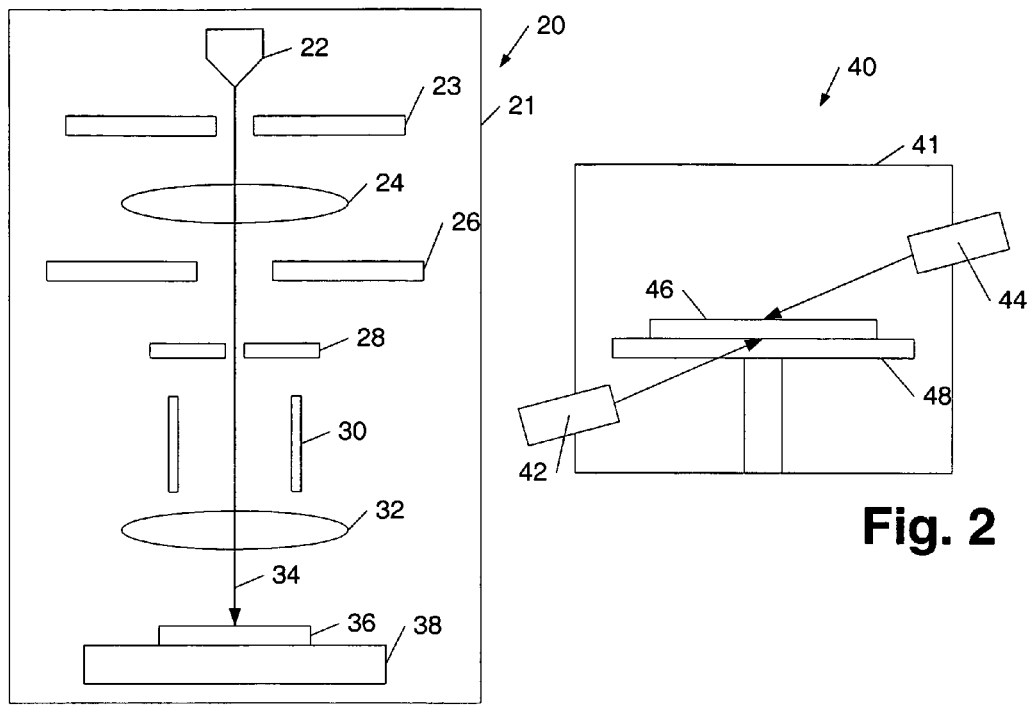
Fig. 1
Fig. 2
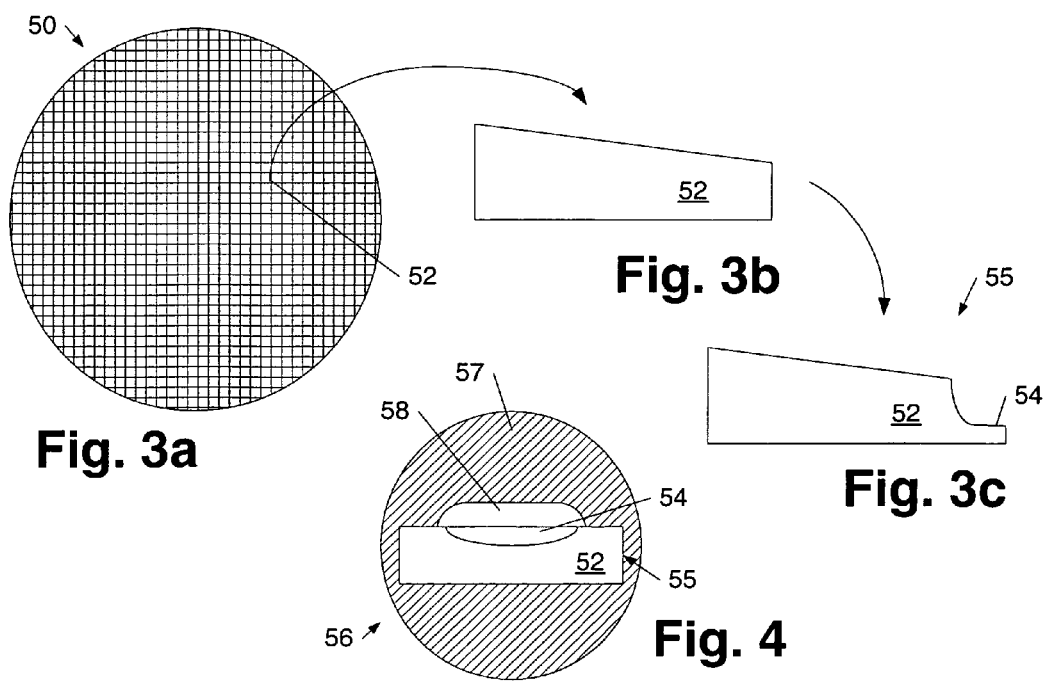
Fig. 3a
Fig. 3b
Fig. 3c
Fig. 4

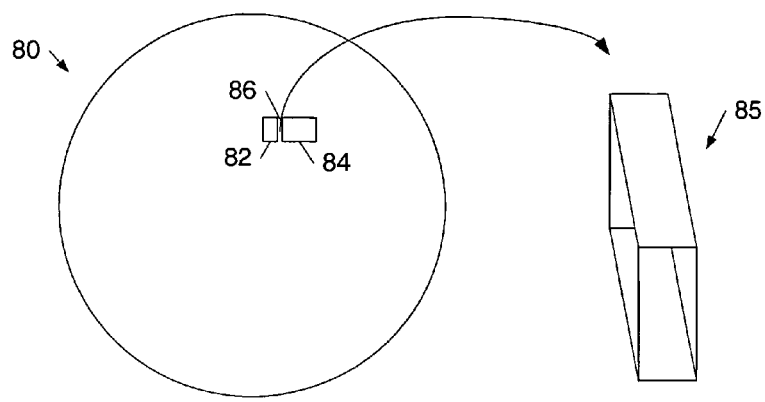
Fig. 6a          Fig. 6b
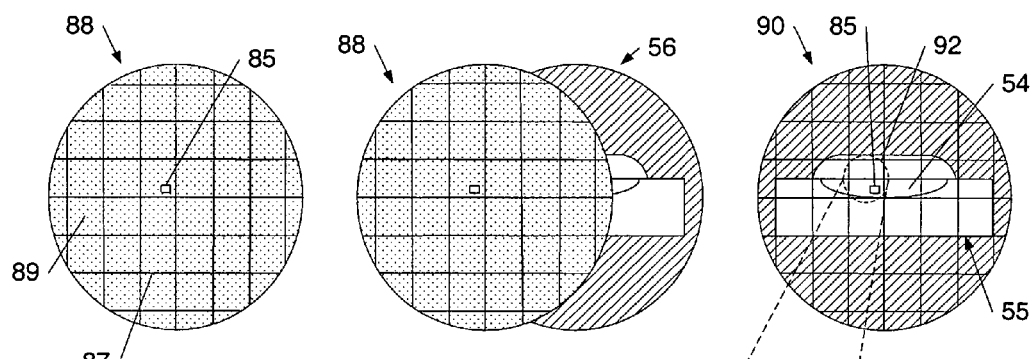
Fig. 7a          Fig. 7b          Fig. 7c
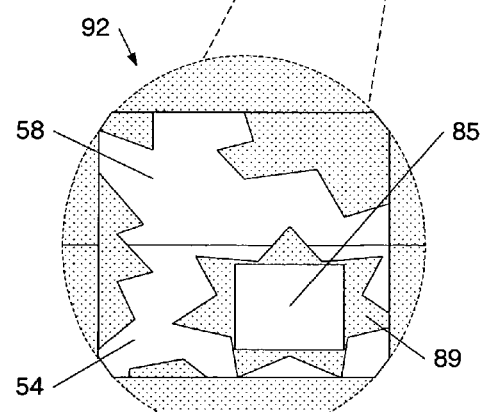
Fig. 7d

METHOD TO PREPARE TEM SAMPLES

PRIORITY APPLICATION

The present application claims priority to provisional application No. 60/494,817 entitled "Method To Prepare TEM Samples," filed Aug. 13, 2003.

BACKGROUND OF THE INVENTION

1. Field of the Invention

This invention relates to semiconductor device metrology, and more particularly, a method for preparing samples for TEM analysis.

2. Description of the Related Art

The following descriptions and examples are not admitted to be prior art by virtue of their inclusion within this section.

Fabricating a microelectronic device with one or more parameters outside the design specifications of the device may hinder or prohibit the function of the device, leading to a reduction in production efficiency and device quality. Consequently, the fabrication of microelectronic devices often includes analyzing microelectronic topographies at different stages of the process to insure that the devices formed therefrom meet their specified functionality requirements. In fact, as production volumes and efforts to improve process control increase in the integrated circuit fabrication industry, the ability to accurately analyze microelectronic processes and the materials associated with such processes in a timely manner becomes more critical. In general, the term "microelectronic topography," as used herein, may refer to a semiconductor substrate having one or more layers formed thereon, regardless of whether a functioning device has been formed from the topography or not. As such, the term "microelectronic topography" may generally refer to a structure used to fabricate a microelectronic device at any given point in the fabrication process. In addition, the "analysis of a microelectronic topography," as used herein, is not restricted solely to analyzing the upper surface of a wafer, but may include analyzing more than one layer and/or the substrate of the topography.

A microelectronic topography may be analyzed for a number of different properties. For example, a microelectronic topography may be analyzed for its electrical properties, composition, and/or physical thickness of individual layers and/or structures, to name just a few. Consequently, a number of different techniques may be used to analyze a microelectronic topography. For example, transmission electron microscopy cross-sectional analysis (hereinafter referred to as "TEM") may be used to analyze a microelectronic topography. TEM generally involves directing an electron beam at a microelectronic topography while a photograph is simultaneously taken. Both the photograph and electron beam are used to analyze the exposed layers.

There are a few different manners with which to prepare the sample of the microelectronic topography for TEM analysis. One manner is referred to herein as the "wedge method." The wedge method involves dicing a wafer into small fragments and polishing two opposing cross-sectional sides of a fragment to a target location. Subsequently, a portion of the polished fragment is etched to form an image region having a thickness of a few thousands angstroms and a large viewing area with which to analyze. Such a process generally offers a good image quality, but is very labor intensive. In particular the polishing process is an intricate and time-consuming process, requiring a highly skillful person to manually polish the sample against a variety of different polishing pads and frequently check whether the target location has been obtained. In addition to obtaining the target location, the polishing processes are used to form the fragment into a wedge-shape such that one end is thicker than an opposing end of the fragment. Although the formation of the wedge-shape provides some support, a sample prepared using this technique is still susceptible to breaking. Furthermore, the wedge method involves dicing an entire wafer into multiple fragments. As a result, the wafer cannot be used for purposes that involve a whole wafer.

Another technique for preparing TEM samples is referred to herein as the "FIB lift out method." The FIB lift out method involves using a relatively high energy focused ion beam to cut a fragment out of a wafer which is generally significantly smaller than the fragment cut out in the wedge method. In particular, the cutting technique employed by the FIB lift out method offers a manner in which to more precisely locate the target location of the wafer and, therefore, does not require the entire wafer to be diced. Consequently, the wafer may be used for other processing or samples. Moreover, the fragment cut out by the FIB lift out method typically only includes a portion of substrate and, therefore, is thinner than the fragment cut out in the wedge method. The thinner fragment is subsequently lifted from the wafer and immediately transferred to a carbon coated copper grid for analysis. In this manner, the FIB lift out method is significantly faster than the wedge method. On the other hand, however, the FIB lift out method does not allow further thinning of the sample to be conducted. In addition, the FIB lift out method causes significant damage to the crystalline structure of the substrate and generally does not produce a quality image or a large viewing area. Moreover, the FIB lift out method redeposits materials along the sidewalls of samples.

It would, therefore, be desirable to develop a method of preparing TEM samples that overcomes the aforementioned problems. In particular, it would be beneficial to form a TEM sample having good image quality without having a thick damaged crystalline structure or a thick redeposited layer. In addition, it would be advantageous to be able to perform energy dispersive spectroscopy (EDS) analysis without the artifact of carbon film. Moreover, it would be beneficial to develop a method for preparing TEM samples in which the thickness of the sample can be thinned for multiple analyses. Furthermore, it would be particularly advantageous for such a method to be fast and uncomplicated.

SUMMARY OF THE INVENTION

The problems outlined above may be in large part addressed by a method for preparing a transmission electron microscopy (TEM) sample which includes removing a portion of a substrate using a focused ion beam tool and securing the removed portion to a support structure to form a grafted structure. The method further includes forming an opening within the support structure to expose an underside of the removed portion and thinning one or more exposed surfaces of the removed portion using an ion beam miller tool. In some cases, the method may include repeating the step of thinning subsequent to analyzing the removed portion with a TEM tool. In some embodiments, the step of thinning may include exposing the grafted structure to an ion beam energy between approximately a few hundred eV and approximately 5 keV. Conversely, the step of removing the portion from the substrate may include directing a focused ion beam having an energy greater than or equal to approximately 30 keV toward the substrate. In some cases, the step of removing the portion of the substrate may include forming first and second trenches on opposing sides of a target location of the substrate and disconnecting the portion of the substrate between the first and second trenches. In some embodiments, the dimensions of the first and second trenches may be substantially similar. In other cases, however, one of the trenches may be formed wider than the other.

The step of securing the removed portion to the support structure may include positioning the removed portion on the support structure in the same upright position as taken from the substrate. In other embodiments, the step of securing the removed portion to the support structure may include flipping the removed portion such that a bottom surface of the removed portion is facing up. Alternatively, the step of securing the removed portion to the support structure may include positioning the removed portion on the support structure such that a cross-section of the removed portion is facing up. In any case, the step of securing the removed portion to the support structure may, in some embodiments, include placing the substrate specimen upon a film which is adhered to a mesh grid. In some case, the substrate specimen may be placed within an opening of a mesh grid and upon a film attached to the mesh grid and spanning an underside of the opening. In other cases, the substrate specimen may be placed upon a film attached to the upper side of a mesh grid. In either case, the step of securing may include positioning the mesh grid upon a framework having the support structure such that the substrate specimen is above the support structure. Subsequent thereto, the step of securing may include pushing the substrate specimen through the film onto the support structure to form a grafted structure. In some cases, the method may further include adhering the substrate specimen to the support structure with a material distinct from the film.

As noted above, the method may include the formation of an opening within the support structure to expose an underside of the removed portion. In particular, the method may include removing a portion of the support structure underlying the substrate specimen subsequent to the step of adhering the substrate specimen to the support structure to expose an underside of the substrate specimen. In some cases, the step of removing the portion of the support structure underlying the substrate specimen may include forming one or more first trenches spaced apart from the substrate specimen through the support structure. Subsequent thereto, the grafted structure may be flipped and one or more additional trenches may be formed in the support structure spaced apart from the substrate specimen and extending from the first trenches to form a cut-out portion within the support structure. At such a point, the method may include flipping the grafted structure again and pushing the cut-out portion of the support structure from the grafted structure.

As a result of the aforementioned method, a TEM sample is provided herein which includes a substrate specimen adhered to and extending across an opening of a support structure. In a preferred embodiment, the opening is sufficiently shallow and wide to allow ion milling beams to reach the substrate specimen through the opening. In some cases, the support structure may be wedge shaped and the substrate specimen may be adhered proximate to a thin edge of the wedge. In other embodiments, the support structure, however, may be formed of other shapes including but not limited to rectangular, square or cylindrical blocks. In some embodiments, the support structure may include a portion of a semiconductor wafer. In addition, the substrate specimen may be a portion of a semiconductor wafer having a microelectronic topography in some cases. In such embodiments, the substrate specimen may be adhered to the support structure such that a cross-section of the microelectronic topography is contact with the support structure. Alternatively, the substrate specimen may be secured to the support structure such that an uppermost layer of the microelectronic topography is in contact with the support structure. In yet other embodiments, the substrate specimen may be secured to the support structure such that an uppermost layer of the microelectronic topography is spaced above the support structure.

There may be several advantages for preparing a TEM sample in the manner described herein. In particular, the method described herein allows a TEM sample having good image quality and good resolution to be prepared in a fast and efficient manner. In addition, the method described herein allows a precise location of a wafer to be prepared and analyzed for TEM analysis as well as multiple samples to be prepared from a dense area of interest in the wafer. Furthermore, the method is not complicated and not highly dependent upon the skill of the operator preparing the sample. Consequently, a higher number and more uniform samples may be prepared. The method described herein further allows energy dispersive spectroscopy analysis to be performed without the artifact of a carbon film. Moreover, the method described herein offers a manner in which a TEM sample may be further thinned while being sufficiently supported.

BRIEF DESCRIPTION OF THE DRAWINGS

Other objects and advantages of the invention will become apparent upon reading the following detailed description and upon reference to the accompanying drawings in which:

FIG. 1 depicts an exemplary configuration of a focused ion beam tool;

FIG. 2 depicts an exemplary configuration of an ion beam miller tool;

FIG. 3a depicts a semiconductor wafer diced into a plurality of semiconductor die;

FIG. 3b depicts one of the semiconductor die from the semiconductor wafer illustrated in FIG. 3a having an edge polished;

FIG. 3c depicts the semiconductor die illustrated in FIG. 3b subsequent to having a portion thinned;

FIG. 4 depicts the semiconductor die illustrated in FIG. 3c arranged upon a supportive framework;

FIG. 6a depicts a substrate having two trenches formed alongside a target portion of the substrate;

FIG. 6b depicts a substrate specimen removed from the target portion of the substrate illustrated in FIG. 6a;

FIG. 7a depicts the substrate specimen illustrated in FIG. 6b arranged upon a mesh grid have a film attached thereto;

FIG. 7b depicts the mesh grid illustrated in FIG. 7a with the substrate specimen arranged thereon arranged above the supportive framework illustrated in FIG. 4;

FIG. 7c depicts the mesh grid illustrated in FIG. 7a with the substrate specimen arranged thereon aligned with the supportive framework illustrated in FIG. 4;

FIG. 7d depicts a magnified view of the aligned set of frameworks illustrated in FIG. 7c after the substrate specimen has been pushed through the film attached to the mesh grid;

Figure 5:
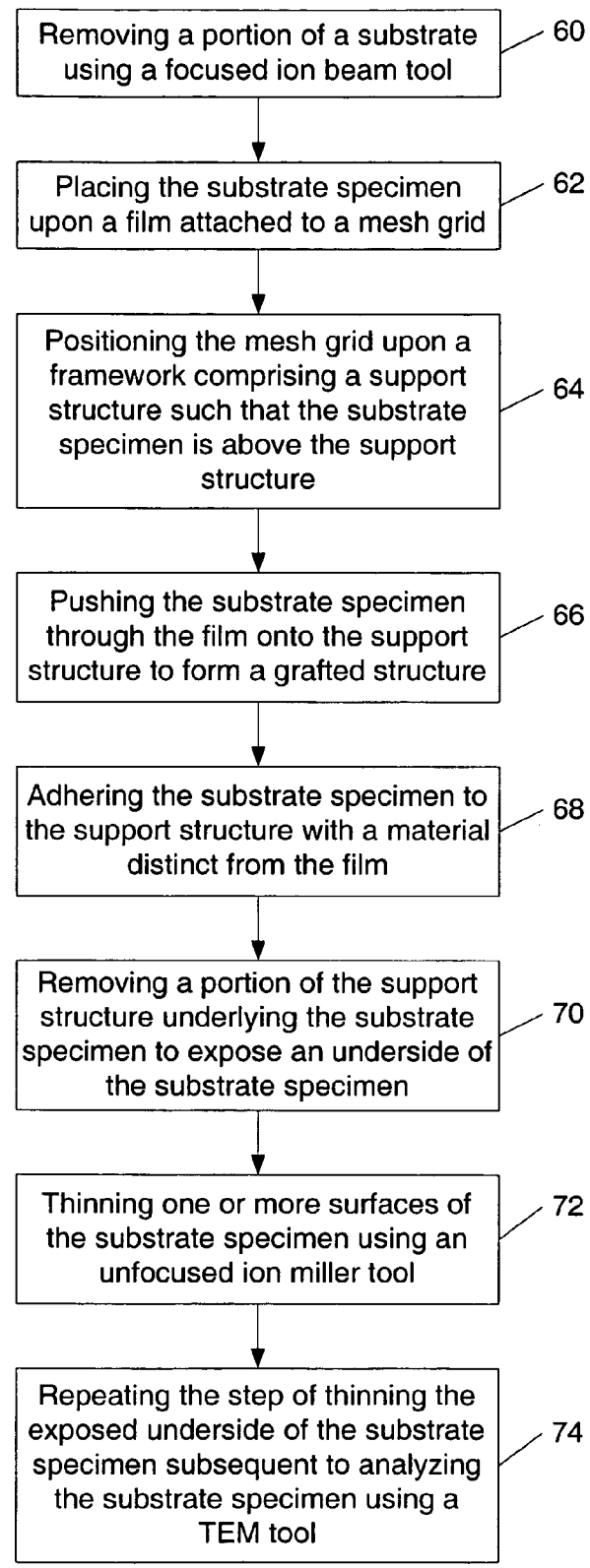
FIG. 5 depicts a flowchart of a method for preparing a TEM sample.

While the invention may include various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning to the drawings, an exemplary method for preparing a TEM sample is shown and described. In addition, exemplary equipment used for the method are shown and described. In particular, FIGS. 1 and 2 illustrate exemplary configurations of focused ion beam (FIB) tool 20 and ion beam miller tool 40, respectively. As will be explained in more detail below, each of the tools is used during specific processes of the method. As shown in FIG. 1, FIB tool 20 may include ion beam emitter 22. In most commercial FIB systems, positively charged gallium ions from liquid metal ion sources are used, however, FIB tool 20 may additionally or alternatively use other ion sources. For example, materials such as silicon, indium, cesium or even gases such as argon, krypton or oxygen can be used as ion sources. FIB tool 20 may further include extraction electrode 23, which is used to extract ion beam 34 from emitter 22. Acceleration electrode 24 accelerates the ion beam to a desired energy and condenser lens electrode 26 adjusts the current of the ion beam to a desired current value. Positioned below condenser lens electrode 26, aperture 28 limits the angular width of the ion beam and deflection electrodes 30 deflect and scan the ion beam into two dimensions. FIB tool 20 may further include objective lens 32 to focus ion beam 34 onto substrate 36. In some cases, the focused ion beam may be used to image substrate 36 by scanning ion microscopy or may be used to process substrate 36, such as by etching or material deposition. In either case, the ion source is generally capable of being focused into a sub one-tenth micron wide beam at substrate 36.

As shown in FIG. 1, FIB tool 20 may include housing 21 such that the interior of the tool may be maintained at a high vacuum during operation. In addition, substrate 36 may be arranged on stage 38 which is capable of adjusting the tilt of the specimen relative to ion beam 34. Although not shown, FIB tool 20 may include power supplies and control units coupled to the plurality of components shown in FIG. 1. In general, the interaction of ion beam 34 with the substrate 36 results in an ejection of secondary electrons and ions from the surface of the specimen. As such, FIB tool 20 may include additional components such as a detector for detecting secondary electrons or ions, a processing circuit for processing an output signal from the detector, a display device for displaying SIM images, and/or other devices connected with the control unit and power supplies. Focused ion beam tools are commercially available from, for example, FEI Company of Hillsboro, Oregon.

Turning to FIG. 2, ion beam miller tool 40 is shown having ion beam emitters 42 and 44 extending within sidewalls of housing 41. During operation, ion beam miller tool 40 is maintained at a high vacuum and an argon ion beam is projected from one or both of ion beam emitters 42 and 44 toward the upper and lower surfaces of substrate 46, respectively. In this manner, ion beam miller tool 40 may be configured to etch the topside and/or the underside of substrate 46. Accordingly, substrate holder 48 may include an opening by which to access underside of substrate 46. As with stage 38 in FIB tool 20, substrate holder 48 in ion beam miller tool 40 is capable of tilting to adjust the angle at which substrate 46 is arranged relative to the ionized argon atoms traveling toward the specimen. In general, ion beam emitters 42 and 44 may be configured to focus an ion source into an ion beam having a width of a few millimeters to tens millimeters. Although ion beam emitters 42 and 44 are shown arranged along the sidewalls of ion beam miller tool 40 in FIG. 2, ion beam emitters 42 and 44 may be arranged at any location with which to project ion beams onto the upper and lower surfaces of substrate 46. In yet other embodiments, ion beam miller tool 40 may only include one ion beam emitter. Ion beam miller tools are commercially available from companies such as Gatan, Inc. of Pleasanton, Calif., for example.

In general, substrates 36 and 46 may include any topography which to image or process. In some embodiments, substrates 36 and 46 may be semiconductor wafers or portions of semiconductor wafers. In some cases, the specimens may include microelectronic topographies including conductive, dielectric and/or semiconductor layers formed upon semiconductor substrates. In other embodiments, substrates 36 and 46 may only include the base semiconductor substrate of a wafer. In yet other embodiments, substrates 36 and 46 may not be semiconductor wafers or portions of semiconductor wafers. In particular, substrates 36 and 46 may be topographies from other industrial applications.

It is noted the configuration of FIB tool 20 and ion beam miller tool 40 are not restricted to the illustration or description discussed in reference to FIGS. 1 and 2. More specifically, FIB tool 20 and ion beam miller tool 40 are shown and described as exemplary systems and, therefore, may include configurations and/or adaptations other than those shown and described reference to FIGS. 1 and 2. For instance, FIB tool 20 may include additional lenses or apertures. In addition or alternatively, ion beam miller tool 40 may include a different arrangement of ion beam emitters 42 and 44 or only one ion beam emitter. Other components or adaptations readily known for enhancing the operation of FIB tool 20 or ion beam miller tool 40 may also be included, depending on the design specifications of the system.

Although ion beam miller tool 40 and FIB tool 20 may be both utilized to etch a specimen through the use of ionized atoms and, consequently, may both be referred to as "ion beam milling" processes, ion beam miller tool 40 and FIB tool 20 are distinct in their operations and capabilities. As noted above, FIB tool 20 may be generally adapted to focus an ion source into a sub one-tenth micron wide beam. In this manner, FIB tool 20 offers an etching process which is selective to specific regions of a specimen. In contrast, ion beam miller tool 40 is not configured to converge the ionized argon atoms produced therein to such an extent. Rather, ion beam miller tool 40 is configured to produce an ion beam having a width on the order of a few to tens of millimeters. As a result, ion beam miller tool 40 has poor selectivity in etching specific regions of substrate 46. Although photoresist materials resistant to the etching characteristics of ion beam miller tool 40 may be used to provide selective etching for substrates, FIB tools have shown to be more effective in etching a precise location. The terms "ion beam miller processes" and "focused ion beam processes" are used herein to respectively refer to processes employing ion beam miller tool 40 and FIB tool 20.

Another difference between ion beam miller tool 40 and FIB tool 20 is FIB tool 20 is generally conducted at higher beam energies than ion beam miller tool 40. In particular, FIB tool 20 is generally conducted with beam energies between approximately 10 keV and approximately 50 keV. In contrast, ion beam miller tool 40 is generally conducted with beam energies between approximately a few hundred eV and 5 keV. As a result, FIB tool 20 tends to etch at a faster rate than ion beam miller tool 40. However, as a consequence, FIB tool 20 tends to create a thick layer of damaged crystalline along the edge of an etched sample. In some cases, the damaged layer may be approximately 20 nm to approximately 100 nm thick. In addition, FIB tool 20 tends to redeposit dust and debris along the edge of an etched sample due to the use of high ion energies. Although FIB tool 20 can be configured to run at ion energies lower than approximately 10 keV, such an adaptation may require additional components to be added to FIB tool 20, increasing the cost and production time to use FIB tool 20. In addition, etching a substrate at lower ion energies drastically affects processing speed. As such, it is undesirable to run FIB tool 20 at low ion energies in many cases. Regardless of the ion energy at which FIB tool 20 is conducted, the focused ion beam process causes an undesirable effect referred to herein as "waterfall line tracing". In embodiments in which a substrate includes a plurality of different materials, the etch characteristics of the focused ion beam may vary with the materials, resulting in a variation of the etch profile along a side of an etched sample resembling a waterfall.

The method described herein uses both FIB tool 20 and ion beam miller tool 40 to prepare a transmission electron microscopy (TEM) specimen. In particular, FIB tool 20 is used for the initial preparation of a substrate sample and ion beam miller tool 40 is used to thin the substrate sample. The specific process parameters utilized by each of the two distinct tools to prepare the TEM specimen are described in more detail below. TEM is accomplished by examining material specimens under a transmission electron microscope. In a transmission electron microscope, a series of electromagnetic lenses direct and focus an accelerated beam of electrons, emitted from an electron gun contained within the microscope, at the surface of a specimen. Electrons transmitted through the specimen yield an image of the specimen's structure which provides information regarding its properties. In addition, elemental and chemical information is provided by both the transmitted electrons and the x-rays that are emitted from the specimen's surface as a result of electron interaction with the specimen. Thus, TEM technology enables materials to be analyzed at near atomic resolution by providing high magnification, high-resolution imaging and analysis capabilities. Because it is necessary for the electron beam to transmit through the specimen, a key component of successful material analysis by TEM techniques is the condition and preparation of the specimen itself. It is noted the terms "specimen" and "sample" referred to herein may be used interchangeably.

As will be explained in more detail below, the method described herein for preparing a TEM sample includes securing a substrate specimen to a support structure and removing a portion of the support structure underlying the substrate specimen such that an underside of the substrate specimen may be thinned by an ion beam miller tool. Although the support structure may be made of a variety of shapes and sizes, it is advantageous for the support structure to be large enough for the TEM sample to be easily and securely handled. In addition, it is advantageous for the support structure to be relatively thin such that ion beams generated in the ion beam miller tool used to thin the substrate specimen may reach the underside of the substrate specimen through the opening formed within the support structure. Moreover, the support structure needs to be made of a material strong enough to support the substrate specimen even when the portion underlying the substrate specimen has been removed. In addition, it is advantageous for the material of the support structure to have an ion beam miller etch selectivity substantially similar to or greater than the substrate specimen. In this manner, the support structure will not be substantially milled away during the thinning process of the substrate specimen.

An exemplary support structure and method for preparing a support structure is illustrated in FIGS. 3a–3c. It is noted that the support structure used for the method described herein is not restricted to the description and structure illustrated in FIGS. 3a–3c. Rather, FIGS. 3a–3c merely offer an exemplary method and structure for supplying a support structure for the TEM specimen prepared using the method described herein. FIG. 3a illustrates semiconductor wafer 50 diced into a plurality of semiconductor die, including semiconductor die 52. As shown in FIG. 3b, one side of semiconductor die 52 may be polished to form a wedged shaped structure. In particular, one side of semiconductor die 52 may be polished such that one side is angled between approximately 5 degrees and approximately 20 degrees relative to its opposing side. Such a range of slope may allow a portion of semiconductor die 52 to be subsequently thinned to provide a region upon which a substrate specimen may be secured while maintaining sufficient stability within the wedged shaped structure to support the substrate specimen, specifically when a portion of the support structure underlying the substrate specimen is removed. Semiconductor die 52, however, may be polished to have a side arranged at larger or smaller angles relative to its opposing side, depending on the size of the support structure and/or the size of the substrate specimen. In other embodiments, two opposing sides of semiconductor die 52 may be polished to form a different shaped structure. In either case, the cross-sectional sides of semiconductor die 52 may be polished or the upper and lower surfaces of semiconductor die 52 (i.e., relative to the orientation of semiconductor wafer 50) may be polished.

Subsequent to polishing semiconductor die 52, a portion of the polished fragment may be etched to form region 54 having a thickness of a few thousand of angstroms and a relatively large area of approximately 0.5 mm by approximately 0.8 mm. Region 54 may be formed to have a larger or smaller thickness and/or a larger or smaller area, depending on the design specifications of the TEM sample. The relatively large area of region 54, however, may allow a portion of region 54 to be easily removed for accessing the underside of a substrate specimen secured to the region. In addition, a thickness of a few thousand angstroms may advantageously allow an opening shallow enough for ion miller beams to access the underside of the substrate specimen for thinning the specimen. Regardless of the dimensions of region 54, the resulting structure shown in FIG. 3c and referenced as numeral 55 may serve as a support structure for a TEM specimen. In some analytical labs, wedge-shaped samples similar to the one described in reference to FIG. 3c are routinely fabricated for analysis, including but not limited to TEM analysis. Consequently, wedge-shaped samples may, in some cases, be plentiful within an analysis lab. As such, in some embodiments, support structure 55 may be a structure that was fabricated for an analysis specimen other than the TEM specimen described herein.

As noted above, the support structure used for the method for preparing a TEM specimen described herein is not limited to the method and structures described in reference to FIGS. 3a–3c. In particular, other methods known in the semiconductor fabrication industry may alternatively be used to form support structure 55. In addition, support structure 55 may be formed to have different dimensions and a different shape. For example, support structure 55 may be a plate having a substantially uniform width. Furthermore, support structure 55 may not be formed from a wafer. In particular, support structure 55 may be formed from a different material which is sufficient to support a substrate specimen and have an ion beam miller etch selectivity substantially similar to or greater than the substrate specimen. Moreover, support structure 55 does not have to be prepared in the laboratory used to prepare the TEM specimen described herein.

Regardless of the manner in which support structure 55 is prepared, support structure 55 may be positioned on a framework for the preparation of the TEM specimen described herein. In particular, support structure 55 may be placed and, preferably secured, to a framework which will be able to support a mesh grid upon which a substrate specimen will be arranged. The framework and the mesh grid will be utilized to graft a substrate specimen onto support structure 55 as described in more detail below in reference to FIGS. 5 and 7a–7d. FIG. 4 illustrates an exemplary framework upon which support structure 55 may be arranged. In particular, FIG. 4 illustrates framework 56 including backing 57 and slot 58. Such a framework may be generally referred to herein as a "slot grid".

As shown in FIG. 4, support structure 55 may be arranged upon framework 56 such that region 54 is aligned over slot 58. Slot 58 is an opening through backing 57 and, therefore, may provide access to region 54 from the underside of framework 56. Such an arrangement may be particularly advantageous for removing a portion of region 54 for the preparation of the TEM specimen as described in more detail below in reference to FIG. 7c. Although slot 58 is elliptically shaped, slot 58 may be any shape and size which allows access to the backside of support structure 55. In addition, framework 56 may, in some embodiments, be a 3 mm circular disk, but framework 56 is not restricted to such a shape or size. Furthermore, backing 57 may be formed from any material sufficient to hold support structure 55 and is substantially more selective to an ion beam milling process than the substrate specimen subsequently arranged upon support structure 55. For instance, backing 57 may include but is not limited to any metal material, such as copper for example.

Turning to FIG. 5, a flowchart of an exemplary method for preparing a TEM sample is outlined. In particular, FIG. 5 outlines a fast and easy method for preparing a TEM sample having good image quality. In addition, the method outlined in FIG. 5 offers a manner with which to prepare a TEM sample which removes a target region of a wafer while allowing other regions of the wafer to remain intact. The method also allows the TEM sample to be thinned multiple times in order for a precise target location of the wafer to be accessed. The method outlined in the flowchart in FIG. 5 is also illustrated as a pictorial succession of steps in FIGS. 6a–9. Accordingly, FIGS. 5 and 6a–9 are discussed concurrently in reference to the steps of the method described herein. It is noted that images depicted in FIGS. 6a–9, as well as FIGS. 1–4, are not drawn to scale. In particular, certain features of the images may be disproportionately sized relative to other aspects of the images to emphasize particular features of the images.

As shown in FIG. 5, the method may include block 60 in which a portion of a substrate is removed. Such a step is represented in FIGS. 6a and 6b, which illustrates the removal of substrate specimen 85 from target portion 86 of substrate 80. In general, block 60 may include any process or number of processes with which to remove a target portion of a substrate. As such, although the specific manner of etching trenches of different widths along the sides of a region comprising the target location and subsequently trimming the trenches to remove the region is described below, the method described herein is not restricted to such a process of cutting out a sample. In addition, the method described herein may include removing substrate regions of any size.

In some cases, it may be advantageous to remove a substrate specimen having relatively small dimensions in order to preserve the remaining regions of the substrate for other samples or for other purposes. In addition or alternatively, it may be desirable to have multiple samples from a small region of a substrate and, therefore, it would be advantageous to minimize the size of the substrate specimen removed for each sample. For example, in some cases, a silver sliver of a wafer having dimensions such as, approximately 8 microns by approximately 25 microns, may be an appropriate size of a substrate specimen to be removed. Substrate specimens having larger or smaller dimensions, however, may be removed as well or alternatively, depending on the TEM analysis to be performed. For example, the width of substrate specimen 85 may be between approximately 0.1 microns and approximately 1.0 micron in some cases. In general, substrate specimens with relatively large dimensions may be less susceptible to breaking, but substrate specimens with relatively small dimensions may require less thinning during the subsequent ion beam mill process. The size of the substrate specimen removed from substrate 80 may be optimized to realize both benefits in a manner sufficient for the TEM specimen being prepared. The depth of the substrate specimen may vary depending on the TEM analysis to be performed and the location of the substrate portion to be analyzed, but may generally range between approximately 100 nm and approximately 1000 nm, and more preferably less than approximately 200 nm.

In some cases, a substrate sample may be removed from a substrate which has not been previously segmented. For example, a substrate sample may be removed from a semiconductor wafer which has not been diced. In this manner, the semiconductor wafer may continue to be used for fabricating circuits or may be used for other processing. In alternative embodiments, a substrate sample may be removed from a portion of a substrate. For example, a substrate sample may be removed from a semiconductor die diced from a semiconductor wafer. In such an embodiment, support structure 55 may be formed from the same wafer as substrate specimen 85. In other cases, however, support structure 55 may be formed from a different wafer than substrate specimen 85 or a material different from a semiconductor wafer.

Prior to block 60, the method may include processes with which to locate target location 86 on substrate 80. For example, the method may include a process with which to locate a layer or structure sought for analysis. In addition, the method may include marking substrate 80 as well as determining the direction to cut substrate 80 to obtain the substrate specimen 85. In some cases, the method may include depositing a protective layer over substrate 80 prior to block 60. Such a protective layer may serve to prevent substrate 80 from chipping during the removal of substrate specimen 85. Some exemplary materials for the protective layer may include but are not limited to tungsten, carbon, and oxide.

As noted above, block 60 may, in some embodiments, include etching trenches along the sides of target portion 86 to remove the portion from substrate 80. In particular, block 60 may include etching trenches 82 and 84 alongside target portion 86. In general, the trenches may be formed by etching the wafer using a relatively high focused ion beam tool, such as FIB tool 20 described in reference to FIG. 1. In this manner, trenches 82 and 84 may be fabricated quickly and with the precision associated with FIB tool 20. In some cases, forming trenches 82 and 84 may include etching substrate 80 using an ion beam greater than or equal to approximately 30 keV. Larger or smaller ion beams, however, may be used for the formation of trenches 82 and 84, depending on the specifications of the TEM sample to be fabricated. In some cases, block 60 may include reducing the beam current of the ion beam for the final cut of trenches 82 and 84. In this manner, the width of the substrate specimen 85 may be more closely managed.

In general, trenches 82 and 84 may be etched into substrate 80 to any depth suitable to obtain the layer or structure to be analyzed. In embodiments in which substrate 80 is a semiconductor wafer, trenches 82 and 84 may be etched to a depth below an upper surface of the semiconductor substrate of the wafer. For example, in some embodiments, trenches 82 and 84 may be etched to a depth a few to several microns below the interface between the semiconductor substrate of the wafer and the first overlying layer. Alternatively, trenches 82 and 84 may be etched to a depth above the semiconductor substrate. In any case, block 60 may further include directing a focused ion beam within one of trenches 82 and 84 to disconnect substrate specimen 85 from the base of trenches 82 and 84. In some embodiments, substrate 80 or, more specifically, the stage upon which substrate 80 is arranged upon may be tilted to aid in directing the focused ion beam within the trench. In addition, block 60 may include lifting substrate specimen 85 from the substrate via a needle. For example, block 60 may include tilting the substrate such that the needle contacts the top and bottom of the substrate specimen 85 and then using the needle to lift the sample from substrate 80.

In some embodiments, trenches 82 and 84 may be formed having substantially similar widths. FIG. 6a, however, illustrates that block 60 may, in some embodiments, include etching trenches of different widths along the sides of target portion 86. In particular, block 60 may include etching narrow trench 82 and wide trench 84 along the sides of target portion 86. In some cases, the width of narrow trench 82 may be between approximately 5 microns and approximately 15 microns and the width of wide trench 84 may be between approximately 20 microns and approximately 30 microns. Trenches having larger or smaller widths may be formed, depending on the depth of the trenches, the depth of substrate specimen 85 to be removed, and the tilting angle of stage 10 within FIB tool 20. In particular, the width of wide trench 84 may need to be larger when the depth of substrate specimen 85 needs to be relatively large and/or if the tilting angle of stage 10 is limited such that a focused ion beam may be directed at a sufficient angle within wide trench 84 to disconnect substrate specimen 85 from substrate 80.

Forming trenches with different widths may advantageously allow more samples to be removed from a given area of substrate 80. In addition, it may allow samples to be removed from a small area of substrate 80. For example, the different width trench technique may allow two portions of a substrate which are only approximately 2 microns apart to be removed from the substrate. The different width trench technique may be particularly applicable with the method of TEM sample preparation described herein since the sides of substrate specimen 85 do not need to be cleaned prior to removal. Conventional TEM sample preparation techniques using a focused ion beam to remove a substrate specimen generally require the sides of the sample to be cleaned prior to disconnecting the specimen from the substrate. Such a cleaning process generally requires the trenches to be sufficiently wide such that the dust and debris created from the FI3 process may be removed. The method described herein, however, includes thinning at least one side of substrate specimen 85 subsequent to its removal from substrate 80. The thinning process removes the dust and debris created from the FIB process used to form trenches 82 and 84 and, therefore, a cleaning process of substrate specimen 85 prior to its removal from substrate 80 is not needed. Consequently, wide trench 84 can be used for allowing a focused ion beam to disconnect the bottom substrate specimen 85 from substrate 80, while narrow trench 82 merely serves to provide the opposite surface from which to disconnect substrate specimen 85.

In any case, block 60 may, in some embodiments, further include trimming trenches 82 and 84 such that the space between the trenches is reduced relative to the spacing originally formed between the trenches. For example, in some cases, the spacing between trenches 82 and 84 may be reduced to a spacing between approximately 0.1 micron and approximately 1.0 micron. As a result, substrate specimen 85 may be removed to have a width between approximately 0.1 micron and approximately 1.0 micron. In some cases, the trimming process may include tilting substrate 80 or, more specifically, the stage upon which substrate 80 is arranged, a few degrees on each side. In yet other embodiments, block 60 may not include a trimming process to remove a portion from a substrate. In particular, an advantage of the method described herein is that a substrate specimen may be thinned subsequent to being removed from a substrate. As such, a substrate specimen does not have to be formed to have a thickness which is needed for TEM analysis upon being removed from a substrate. Such a respite in the thickness of a removed portion may advantageously reduce the amount of time and accuracy needed by an operator of a FIB tool to remove a portion from a substrate.

Returning to FIG. 5, the method for preparing a TEM specimen may include block 62 in which the substrate portion removed in block 60 is placed upon a film attached to a mesh grid. Such a step is represented in FIG. 7a which illustrates substrate specimen 85 secured to mesh grid 88. As shown in FIG. 7a, mesh grid 88 includes film 89 and beams 87. In general, beams 87 may include a material sufficient to support an item large enough to span the spacings of the beams. For instance, beams 87 may include copper or any other metal. Film 89 may include a material sufficient to rupture upon the application of pressure thereto. For example, film 89 may include carbon or a thin layer of oxide. In some cases, it may be particularly advantageous for film 89 to include carbon due to its relative adhesive properties as explained in more detail below in reference to FIG. 7d.

In general, film 89 may be adhered to one side of mesh grid 88. In some cases, substrate specimen 85 may be placed upon the side of mesh grid 88 to which film 89 is attached. In such embodiments, particular care should be taken to insure substrate specimen 85 is positioned above a spacing between beams 87. In alternative embodiments, substrate specimen 85 may be placed on the side of mesh grid which film 89 is not attached. In this manner, substrate specimen 85 may be placed within an opening of structure grid 87 and upon a portion of film 89 spanning an underside of the opening as shown in FIG. 7a. The placement of substrate specimen 85 on such a side of mesh grid 88 may be advantageous for insuring substrate specimen 85 is not arranged above beams 87. In some embodiments, substrate specimen 85 may be rotated prior to being positioned upon film 89. More specifically, the top of substrate specimen 85 referring to the upper surface of substrate 80 may be placed upon film 89. In other embodiments, one of the cross-sectional etched sides of substrate specimen 85 may be placed upon film 89. In yet other embodiments, the bottom of substrate specimen 85 may be arranged upon film 89. In embodiments in which substrate specimen 85 is a specimen of a semiconductor topography, the top of substrate specimen 85 may refer to the surface of substrate 80 arranged furthest from the semiconductor substrate of the wafer, while the bottom of substrate specimen 85 may refer to the semiconductor substrate of the sample.

As shown in FIG. 5, the method described herein may continue to block 64 in which the mesh grid which the substrate specimen was placed upon in block 62 is positioned upon a framework comprising a support structure such that the substrate specimen on the mesh grid is above the support structure. Such a step is represented in FIGS. 7b and 7c, which illustrate mesh grid 88 positioned over slot grid 56, resulting in merged grids 90. In particular, FIG. 7b illustrates the transitory stage of positioning mesh grid 88 over slot grid 56. FIG. 7c illustrates merged grids 90 in which substrate specimen 85 is arranged over region 54 of support structure 55. In some cases, mesh grid 88 and slot grid 56 may be clamped together to form merged grids 90. The dotted pattern depicting film 89 of mesh grid 88 is not illustrated in FIG. 7c so that the placement of substrate specimen 85 over region 54 may be shown. Film 89, however, may be included in merged grids 90 at this point in the process. As noted above, it may be particularly advantageous to position substrate specimen 85 over the thinnest region of support structure 55 (i.e. region 54) such that an opening shallow enough for ion miller beams to access the underside of the substrate specimen may be formed as described below in reference to FIG. 8e.

As shown in FIG. 5, the method described herein may continue to block 66 in which the substrate specimen positioned on the film of the mesh grid is pushed through the film onto the support structure arranged upon the slot grid. More specifically, block 66 may include directing a manipulator needle to push the substrate specimen through the film attached to the mesh grid such that the substrate specimen is arranged upon the underlying support structure. Such a process forms a grafted structure in which the substrate specimen is secured to the support structure. The process corresponding to block 66 is represented in FIG. 7d, which illustrates magnified image 92 of merged grids 90 showing substrate specimen 85 pushed through film 89 onto region 54 of support structure 55. As noted above, in some cases, it may be advantageous for film 89 to include carbon for its adhesive properties. In this manner, substrate specimen 85 may be affixed to support structure 55 when the substrate specimen is pushed through the film. Although carbon may offer beneficial adhesive properties, carbon is susceptible to being removed during a subsequent ion beam milling process and, therefore, it is advantageous to secure substrate specimen 85 to support structure 55 in an additional manner. Block 68 depicts such a process in the method outlined in the flowchart of FIG. 5. In particular, block 68 includes adhering the substrate specimen to the support structure with a material distinct from the film attached to the mesh grid. Such a process is represented in FIGS. 8a and 8b which illustrate magnified portion 96 of grafted structure 94 having securement structures 97 arranged along the ends of substrate specimen 85.

In general, securement structures 97 may include any material sufficient to securely adhere substrate specimen 85 to support structure 55 and has a greater etch selectivity to ion beam milling than the materials of substrate specimen 85 and support structure 55. In this manner, securement structures 97 will not substantially disintegrate during the subsequent thinning process of substrate specimen 85. In order to realize the aforementioned properties, the material used for securement structures 97 may be dependent on the materials included within substrate specimen 85 and support structure 55. For instance, in an embodiment in which substrate specimen 85 and support structure 55 include materials of a microelectronic topography, securement structures 97 may include a metal material, such as tungsten or a tungsten alloy. Other materials, however, may be used as well or alternatively, depending on the design specifications of the TEM specimen being fabricated. In some cases, securement structures 97 may be deposited using a FIB tool, such as FIB tool 20 depicted in FIG. 1. In other embodiments, securement structures 97 may be deposited using other physical vapor deposition or chemical vapor deposition techniques known in the microelectronics fabrication industry.

Figure 8A:
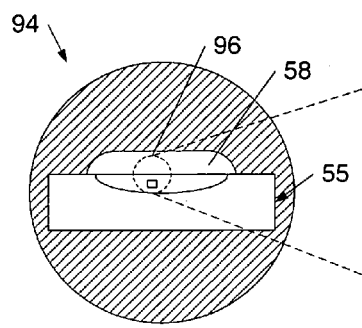
FIG. 8a depicts the aligned set of frameworks illustrated in FIG. 7c after the substrate specimen has been pushed through the film attached to the mesh grid.
Figure 8B:
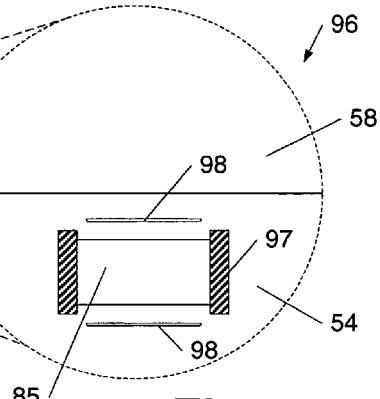
FIG. 8b depicts a magnified view of the aligned set of frameworks illustrated in FIG. 8a after securement structures have been formed at the ends of the substrate specimen and a first set trenches have been formed spaced apart from the substrate specimen.

Grafted structure 94 in FIG. 8a resulting from securement structures 97 being deposited on the ends of substrate specimen 85 is illustrated without mesh grid 88. In particular, beams 87 and film 89 attached to beams 87 are not shown in FIG. 8a. In some embodiments, mesh grid 88 (i.e., beams 87 and remaining portions of film 89 attached to beams 87) may be removed prior to adhering securement structures 97 to substrate specimen 85. In other cases, mesh grid 88 may be removed subsequent to adhering securement structures 97 to substrate specimen 85. As such, in some embodiments, grafted structure 94 depicted in FIG. 8a may include mesh grid 88.

Returning to FIG. 5, the method may further include block 70 in which a portion of the support structure underlying the substrate specimen is removed to expose an underside of the substrate specimen. The process corresponding to block 70 is represented in FIGS. 8b–8e in which a portion of region 54 of support structure 55 underlying substrate specimen 85 is removed to expose an underside of the substrate specimen. The removal process starts with the formation of trenches 98 spaced apart from the substrate specimen 85 as shown in FIG. 8b. In general, trenches 98 may be formed by a focused ion beam tool to insure the precise location of the trenches. Preferably, trenches 98 are sufficiently spaced apart from substrate specimen 85 such that substrate specimen 85 is not etched during the formation of the trenches. An exemplary range of spacing between trenches 98 and substrate specimen 85 may be between approximately 5 microns and approximately 20 microns. Larger or smaller spacings, however, may be used, depending on the design specifications of the TEM sample being fabricated. The lengths of trenches 98 are preferably less than the length of substrate specimen 85. For example, in an embodiment in which substrate specimen 85 has a length of approximately 25 microns, the lengths of trenches 98 may be approximately 20 microns. In this manner, a portion of support structure 55 may be removed without removing substrate specimen 85 from the TEM sample. Trenches 98 are etched through support structure 55 to form openings therethrough. The openings serve to mark the location of substrate specimen 85 for the formation of trenches 100 shown in FIG. 8c.

Figure 8C:
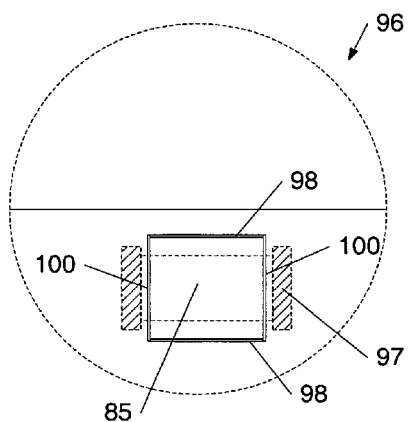
FIG. 8c depicts a magnified view of the aligned set of frameworks illustrated in FIG. 8a flipped over and subsequent to a formation a second set of trenches perpendicular to the first set of trenches.

As shown in FIG. 8c, trenches 100 are formed perpendicular and along the ends of trenches 98. In this manner, a distinct portion of support structure 55 may be separated from the rest of support structure 55. As with the formation of trenches 98, trenches 100 may be formed by a focused ion beam tool to insure their precise location. FIG. 8c depicts substrate specimen 85 and securement structures 97 outlined in dotted lines to indicate that they are positioned below support structure 55. Prior to etching trenches 100, grafted structure 94 may be removed from FIB tool 20, flipped, and placed back into FIB tool 20 such that substrate specimen 85 is facing downward. In this manner, trenches 100 may be formed without etching substrate specimen 85. Various parameters of FIB tool 20 may be adjusted to prevent substrate specimen 85 from being etched through during the formation of trenches 100 and are known to those skilled in the art of focused ion beam etching.

Figure 8D:
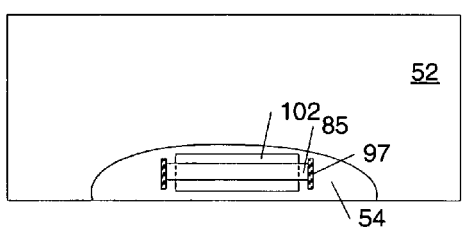
FIG. 8d depicts a top view of the substrate specimen arranged upon the semiconductor die illustrated in FIG. 3c subsequent to the removal of the cut-out portion outlined by the first and second set of trenches.
Figure 8E:
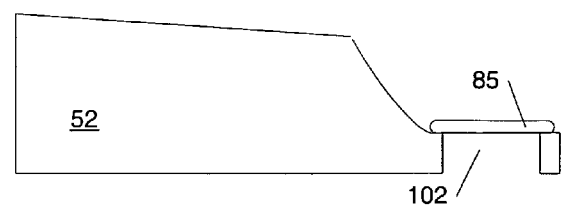
FIG. 8e depicts a side view of the substrate specimen arranged upon the semiconductor die illustrated in FIG. 3c subsequent to the removal of the cut-out portion.

Subsequent to forming trenches 100, grafted structure 94 may be removed from the FIB tool and flipped over such that substrate specimen 85 is facing upward. At this point, the portion of support structure 55 separated by trenches 98 and 100 may be pushed out by a probe needle. FIGS. 8d and 8e illustrate cut-out portion 102 underlying substrate specimen 85 resulting from the removal of the separated portion of support structure 55 from grafted structure 94. As shown in FIG. 8e, the underside of substrate specimen 85 is exposed by cut-out portion 102. FIGS. 8d and 8e illustrate the grafted structure of substrate specimen 85 secured to support structure without slot grid 56 to emphasize the removal of cut-out portion 102 relative to substrate specimen 85. In some embodiments, the grafted structure is maintained upon slot grid 56 for the subsequent thinning process of substrate specimen 85. In other cases, however, the grafted structure may be transferred to another framework which allows ion beams to access the underside of substrate specimen 85. It is noted that the method for forming cut-out portion 102 described in reference to FIGS. 8b–8e is exemplary. Other methods for removing a portion of support structure 55 underlying substrate specimen 85 may alternatively be used in the method described herein. As noted above, the opening within support structure 55 (i.e., cut-out portion 102) is preferably shallow and wide enough to allow ion milling beams to reach substrate specimen 85 through the opening for the thinning process of the substrate specimen.

Figure 9:
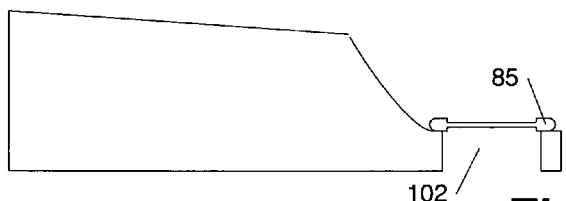
FIG. 9 depicts a side view of the grafted structure illustrated in FIG. 8e flipped over and after a portion of the substrate specimen exposed through the cut-out portion has been thinned.

As shown in FIG. 5, the method for forming a TEM sample may continue to block 72 in which one or more exposed surfaces of the substrate specimen is thinned using an ion beam miller tool. Such a step is represented in FIG. 9 where grafted structure 94 is shown with substrate specimen 85 thinned. Such a process may be performed by an ion beam miller tool, such as ion beam miller tool 40 depicted in FIG. 2. In any case, the thinning process may be performed at an ion energy between approximately a few hundred eV and approximately 5 keV. However, larger or smaller ion energies may be used to thin substrate specimen 85 in other cases. Using a relatively low ion energy may advantageously remove the damaged crystalline layers of substrate specimen 85 without generating substantial further damage to the topography. In addition, the ion beam miller process will generate considerably less dust and debris than a focused ion beam milling process and, consequently, a clearer image may be produced during TEM analysis. Furthermore, the sample may be viewed in a scanning mode due to the clearer image.

In general, the thinning process referred to in block 72 may reduce the thickness of substrate specimen 85 to an amount between a few hundred angstroms and a few thousand angstroms, depending on the analysis to be performed. Often, for failure analysis purposes, a sample needs to be analyzed at a plurality of different thicknesses. In addition, different analysis TEM techniques may necessitate different thicknesses of a sample. As such, in some embodiments, it may be particularly advantageous to be able to thin substrate specimen 85 multiple times. More specifically, it may be advantageous to thin substrate specimen 85 to a desired thickness, analyze the sample by TEM, and subsequently thin the substrate specimen 85 to a different desired thickness for a second TEM analysis. The inclusion of such a provision in the method described herein is illustrated in FIG. 5 as block 74. In particular, block 74 includes repeating the step of thinning one or more exposed surfaces of the substrate specimen subsequent to analyzing the substrate specimen using a TEM tool. The process of thinning and analyzing a substrate specimen may be reiterated any number of times.

A further advantage of the method described herein is that a high image quality TEM sample may be formed without the artifact of carbon film. In particular, a TEM sample may be formed which does not include carbon. As a result, TEM analysis may be formed without having to pass an electron beam through a carbon film to analyze the sample. Such a consequence may be particularly advantageous for compositional analysis techniques, such as energy dispersive spectroscopy (EDS). In particular, the compositional analysis may be more accurate since the carbon film will not interfere with the results.

It will be appreciated to those skilled in the art having the benefit of this disclosure that this invention is believed to provide a method of preparing a TEM sample. Further modifications and alternative embodiments of various aspects of the invention will be apparent to those skilled in the art in view of this description. For example, the method of cutting out a target portion from a wafer is not limited to the method described herein which includes etching trenches alongside a target location. It is intended that the following claims be interpreted to embrace all such modifications and changes and, accordingly, the drawings and the specification are to be regarded in an illustrative rather than a restrictive sense.

What is claimed is:

1. A method for preparing a transmission electron microscopy (TEM) specimen, comprising:
   removing a portion of a substrate using a focused ion beam tool;
   securing the removed portion to a support structure;
   forming an opening within the support structure to expose an underside of the removed portion subsequent to the step of securing the removed portion to the support structure; and
   thinning one or more exposed surfaces of the removed portion using an ion beam miller tool.

2. The method of claim 1, wherein the step of securing the removed portion to a support structure forms a grafted structure comprising the removed portion and the support structure, and wherein the step of thinning the exposed underside comprises exposing the grafted structure to an ion beam energy between approximately a few hundred eV and approximately 5 keV.

3. The method of claim 1, wherein the step of removing the portion of the substrate comprises directing a focused ion beam having an energy greater than or equal to approximately 30 keV toward the substrate.

4. The method of claim 1, wherein the step of securing the removed portion to the support structure comprises flipping the removed portion such that a bottom surface of the removed portion is facing up.

5. The method of claim 1, wherein the step of securing the removed portion to the support structure comprises positioning the removed portion on the support structure such that a cross-section of the removed portion is facing up.

6. The method of claim 1, further comprising repeating the step of thinning subsequent to analyzing the removed portion using a TEM tool.

7. The method of claim 1, wherein the step of removing the portion of the substrate comprises:
   forming a first trench within the substrate on one side of a target location of the substrate;
   forming a second trench within the substrate on another side of the target location, wherein the second trench is wider than the first trench; and
   disconnecting the portion of the substrate between the first and second trench from the substrate.

8. A method for preparing a transmission electron microscopy (TEM) sample, comprising:
   placing a substrate specimen upon a film attached to a mesh grid;
   positioning the mesh grid upon a framework comprising a support structure such that the substrate specimen is above the support structure; and
   pushing the substrate specimen through the film onto the support structure to form a grafted structure.

9. The method of claim 8, further comprising adhering the substrate specimen to the support structure subsequent to the step of pushing the substrate specimen through the film with a material distinct from the film.

10. The method of claim 9, further comprising removing a portion of the support structure underlying the substrate specimen subsequent to the step of adhering the substrate specimen to the support structure to expose an underside of the substrate specimen.

11. The method of claim 10, wherein the step of removing the portion of the support structure underlying the substrate specimen comprises:
    forming one or more first trenches spaced apart from the substrate specimen through the support structure;
    flipping the grafted structure;
    forming one or more second trenches in the support structure spaced apart from the substrate specimen and extending from the first trenches to form a cut-out portion within the support structure; and
    pushing the cut-out potion of the support structure from the grafted structure.

12. The method of claim 10, further comprising exposing the grafted structure to an ion beam milling environment to thin one or more exposed surfaces of the substrate specimen.

13. The method of claim 8, wherein the step of placing the substrate specimen upon the film comprises placing the substrate specimen within an opening of the mesh grid, wherein the film is attached to the mesh grid and spans an underside of the opening.

14. A transmission electron microscopy (TEM) sample, comprising:
    a support structure comprising an opening; and
    a substrate specimen adhered to the support structure and extending across the opening, wherein the opening is sufficiently shallow and wide to allow ion milling beams to reach the substrate specimen through the opening, wherein the support structure comprises a wedge shape, and wherein the substrate specimen is adhered proximate to a thin edge of the wedge.

15. The TEM sample of claim 14, wherein the support structure comprises a portion of a semiconductor wafer.

16. The TEM sample of claim 14, wherein the substrate specimen is a portion of a semiconductor wafer comprising a microelectronic topography.

17. The TEM sample of claim 16, wherein the substrate specimen is adhered to the support structure such that a cross-section of the microelectronic topography is in contact with the support structure.

18. The TEM sample of claim 16, wherein the substrate specimen is secured to the support structure such that an uppermost layer of the microelectronic topography is in contact with the support structure.

19. The TEM sample of claim 16, wherein the substrate specimen is secured to the support structure such that an uppermost layer of the microelectronic topography is spaced above the support structure.

20. The TEM sample of claim 14, wherein a portion of the thin edge of the wedge to which the substrate specimen is adhered comprises a thickness between approximately 2000 angstroms and approximately 3000 angstroms.

* * * * *